(12) United States Patent
Grinberg et al.

(10) Patent No.: US 10,518,088 B2
(45) Date of Patent: Dec. 31, 2019

(54) METHOD OF ADAPTIVE ELECTRIC ACTION ON A LIVING ORGANISM (VARIANTS)

(71) Applicants: Yakov Zalmanovich Grinberg, Taganrog (RU); Yury Yurievich Starovoytov, Rostov-on-Don (RU); Mikhail Anatolievich Unakafov, Taganrog (RU)

(72) Inventors: Yakov Zalmanovich Grinberg, Taganrog (RU); Yury Yurievich Starovoytov, Rostov-on-Don (RU); Mikhail Anatolievich Unakafov, Taganrog (RU)

(73) Assignee: RITM OKB ZAO, Taganrog (RU)

( * ) Notice: Subject to any disclaimer, the term of this patent is extended or adjusted under 35 U.S.C. 154(b) by 0 days.

(21) Appl. No.: 15/778,519

(22) PCT Filed: May 11, 2016

(86) PCT No.: PCT/RU2016/000280
§ 371 (c)(1),
(2) Date: May 23, 2018

(87) PCT Pub. No.: WO2017/095260
PCT Pub. Date: Jun. 8, 2017

(65) Prior Publication Data
US 2018/0369585 A1    Dec. 27, 2018

(30) Foreign Application Priority Data

Dec. 1, 2015    (RU) ................................ 2015151655

(51) Int. Cl.
*A61N 1/00*    (2006.01)
*A61N 1/36*    (2006.01)

(52) U.S. Cl.
CPC ..... *A61N 1/36031* (2017.08); *A61N 1/36014* (2013.01); *A61N 1/36034* (2017.08);
(Continued)

(58) Field of Classification Search
CPC .. A61N 1/36; A61N 1/36031; A61N 1/36034; A61N 1/36178; A61N 1/36192; A61N 1/36196
See application file for complete search history.

(56) References Cited

U.S. PATENT DOCUMENTS

2007/0293918 A1* 12/2007 Thompson ......... A61N 1/36021
607/72

FOREIGN PATENT DOCUMENTS

RU    2135226 C1    8/1999
RU    2325930 C2    6/2008

* cited by examiner

*Primary Examiner* — Mallika D Fairchild
(74) *Attorney, Agent, or Firm* — Nadya Reingand; Yan Hankin

(57) ABSTRACT

The invention comprises SCENAR-therapy or other methods of electric stimulation, where an inductive energy storage unit is used to generate stimuli, and can be applied for therapeutic, rehabilitation, research, and preventive purposes. The invention includes applying electrodes on tissues and transmitting through them bursts of electrical stimuli. The stimuli are controlled based on processes occurring in these tissues as a result of their interaction with the electrical stimuli. The exposure duration and/or stimuli parameters are controlled according to the free oscillation parameters. The invention includes three types of parameter measurements: measuring parameters while the current stimulus burst is acting; measuring parameters of the last stimulus of each burst; and generating a probing sole stimulus before the main burst and measuring parameters of this stimulus. In all (Continued)

three cases, the exposure duration and/or the parameters of the subsequent stimuli are controlled based on the results of these measurements.

21 Claims, 8 Drawing Sheets

(52) U.S. Cl.
CPC ..... *A61N 1/36178* (2013.01); *A61N 1/36192* (2013.01); *A61N 1/36196* (2013.01)

11  12  13        14

METHOD OF ADAPTIVE ELECTRIC ACTION ON A LIVING ORGANISM (VARIANTS)

CROSS-REFERENCE TO RELATED PATENT APPLICATIONS

The present patent application is a National stage patent application from the PCT patent application PCT/RU2016/000280 filed May 11, 2016 which claims priority Russian application RU2015151655 filed Dec. 1, 2015.

FIELD OF THE INVENTION

The invention relates to physical therapy, in particular, to the methods of electric pulse stimulation of a living body (hereinafter—electric stimulation), and specifically to SCENAR-therapy or other methods of electric stimulation, where an inductive energy storage unit is used to generate stimuli, and can be applied for therapeutic, rehabilitation, and preventive purposes, as well as in making research related to the study of the electric stimulation effect on a living body.

BACKGROUND

There is a great number of patents that describe methods and technical means for SCENAR-therapy (for example, the following RU patents: 2325929, 2325930, 2155614, 2161904, 2211712, 2113249 etc.) as well as treatment options for various diseases that include SCENAR-therapy (see, for example, RU patents: 2405595, 2377032, 2344852, 2380124, 2294216, 2250785, 2175564, 2296551, 2285550, 2212907).

There is a method of electric stimulation of biological tissues by stimuli supplied through electrodes, monitoring the tissue response to the stimuli and controlling the stimulus width and amplitude based on the tissue response of the biological object (see International Application WO0209809A1, A61N1/36 published on 7 Feb. 2002).

In this method of electric pulse stimulation, single stimuli are used, and stimulus width (duration) and amplitude are controlled based on the tissue response. Generating the stimuli without an inductive energy storage unit makes the parametric control of their waveform impossible, and controlling only two stimulus parameters narrows down the opportunities for optimizing the stimulation according to the tissue response as well as the functionality of electric stimulation, and, as a result, its effectiveness decreases.

There is a method of electric stimulation that involves exposing tissues of a biological object to stimuli supplied through electrodes and controlling stimulus duration according to the estimated electrophysiological parameters of interelectrode tissues, with the measurements taken during the exposure of the biological object to the electric stimulation (see International Application WO1990010472 A1, A61N1/36, published on 20 Sep. 1990).

There is also a method of SCENAR therapy (disclosed in RU patent 2355443, A61N1/36, published on 20 May 2009) which includes the exposure of a biological object's tissues to the stimuli generated using an inductive energy storage unit and supplied to the said tissues through electrodes, excitation (due to the said effect) of electric oscillations in the biological tissues between the electrodes, and the adaptive control of stimulus duration in accordance with the body response to the electric stimulation, excluding the occurrence of pain during SCENAR-therapy.

In these SCENAR-therapies the tissues of a biological object are exposed to single stimuli and only the stimulus duration (or frequency and duration) is (are) controlled. This makes it impossible to control the waveform of a single stimulus and the parameters of stimulus bursts, which reduces the extent of exposure optimization according to the body's response and the narrows down the functionality of electric stimulation.

In terms of technical essence, the closest to the claimed method is the method of electric stimulation adopted for the prototype, comprising the exposure of tissues of a biological object to the stimuli generated using an inductive energy storage unit and supplied to these tissues through electrodes, excitation (due to the said effect) of electric oscillations in the oscillating circuit formed by the inductance of the said inductive energy storage unit and the impedance of interelectrode tissues, and controlling the duration of electric stimulation and/or the stimulus waveform according to the electrochemical processes in the biological tissues exposed to the stimuli (see RU patent 2325929, IPC A61N1/08 A61N1/36, published on 10 Jun. 2008).

The disadvantage of the prototype method is the impossibility of controlling the stimuli based on the current values of the electrical oscillation parameters and, in particular, the lack of synchronization of the next stimulus with the phase of free oscillations of the previous stimulus in the burst. Consequently, the adaptation of the electrical stimulation to the condition of the stimulated tissues and the functionality of electric stimulation decrease, which results in reduced effectiveness of electric pulse therapy. In this case, the patient may have pain when exposed to electric stimuli, which impairs the comfort of therapy.

SUMMARY

The task of this group of inventions is to develop an electric stimulation method that provides adaptive control of stimuli based on the ongoing values of oscillation parameters, thereby improving the adaptation of the electric stimulation to the condition of the stimulated tissues, and to enhance the functionality of electric stimulation.

This task is solved as follows: in the method of electric stimulation where the electrodes are applied on the tissues of a biological object, and the bursts of electrical stimuli generated by an inductive energy storage unit, are supplied through these electrodes, the parameters of free oscillations are measured during the exposure, and the exposure duration and parameters of the stimulus bursts are controlled according to the measured oscillation parameters.

The claimed method of electric stimulation may be implemented in a variant according to which the oscillation parameters are measured during the action of the current stimulus burst and, according to these measurements, one controls the exposure duration and/or the parameters of the stimuli in the same burst and/or in the next burst and/or in any of the subsequent stimulus bursts, and/or the repetition rate of subsequent stimulus bursts.

The claimed method of electric stimulation may be implemented in a variant according to which the oscillation parameters are measured during the last stimulus of each burst and, according to these measurements, one controls the exposure duration and/or the stimulus parameters in the next stimulus burst or in any of the subsequent stimulus bursts and/or the repetition rate of subsequent stimulus bursts.

Finally, the claimed method of electric stimulation may be implemented in a variant according to which, at the end of each burst and before the next one, an additional probing stimulus is generated, while the oscillations parameters are measured during the exposure of the biological object's tissues to the probing stimulus and, according to these measurements, one controls the exposure duration and/or the stimulus parameters in the next stimulus burst or in any of the subsequent stimulus bursts and/or the repetition rate of subsequent stimulus bursts.

In addition, in any of the above embodiments of the claimed method of electric stimulation, they take the number of stimuli in the burst, and/or the time interval between the adjacent stimuli in the burst, and/or the stimulus waveform, as the stimulus parameters to be controlled.

Moreover, in any of the embodiments of the claimed method of SCENAR therapy, they use an inductance coil or transformer or autotransformer as an inductive energy storage unit.

The technical result from the use of the invention is an increased effectiveness and comfort of the electric stimulation.

This result is achieved due to the application of stimulus bursts, due to estimation of the oscillation parameters in the oscillating circuit, and controlling the parameters of the burst stimuli and/or the repetition rate of stimulus bursts according to the monitored parameters of these oscillations. The adaptive stimulus control enhances the functionality of electric stimulation, makes it possible to select the optimal structure the acting stimulus for the therapy, improves the adaptation of the electric stimulation to the tissue response of the biological object, and thus results in an increased therapeutic effect of the stimulation and less probable or reduced pain in the patient, which ultimately provides a more effective and more comfortable electric stimulation.

BRIEF DESCRIPTION OF THE DRAWINGS

The essence of the invention is illustrated by the following drawings.

DETAILED DESCRIPTION OF THE PREFERRED EMBODIMENT

Figure 1:
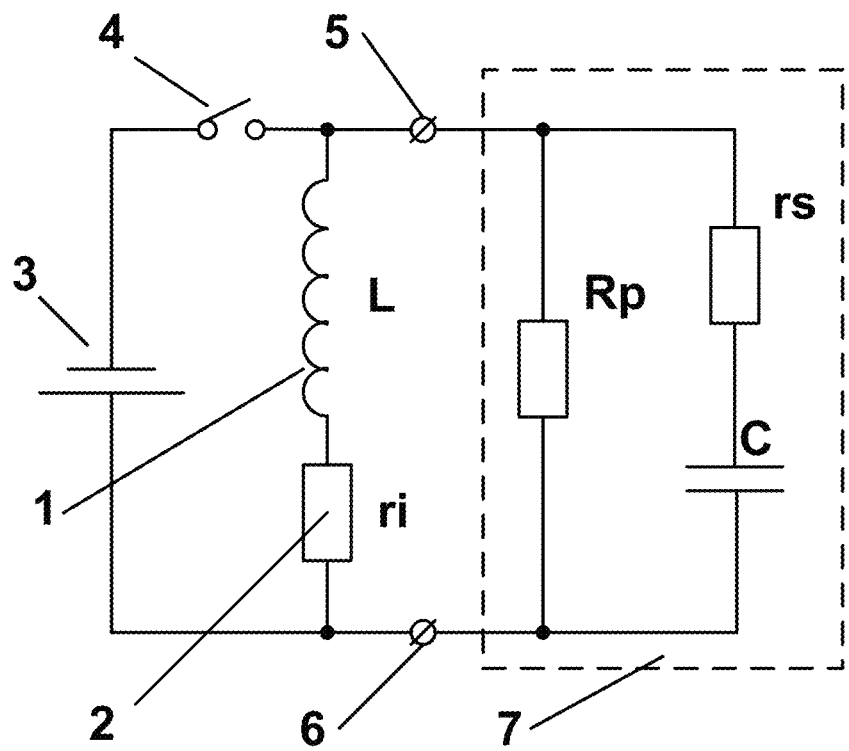
FIG. 1 is a functional diagram of the output stage of the SCENAR device and the electrical equivalent of the interelectrode tissues of the biological object.

The proposed method of electric stimulation can be implemented, for example, using SCENAR-1-NT neuroadaptive electric stimulator (hereinafter—SCENAR device). The functional diagram of the output stage of the SCENAR device includes an inductive energy storage unit 1 (FIG. 1) with an internal active resistance 2 connected to the power source 3 via a switch 4 and to the electrodes 5 and 6 that are applied on the tissues of a biological object, whose electrical equivalent is represented by the RC-circuit 7 (see "Methods of Clinical Neurophysiology," edited by V. B. Grechina, Leningrad, Nauka, 1977, pp. 7-8), and includes the resistance $R_p$ and the double-layer capacitance C, as well as the resistance $r_s$ of the interelectrode tissues.

Figure 2:
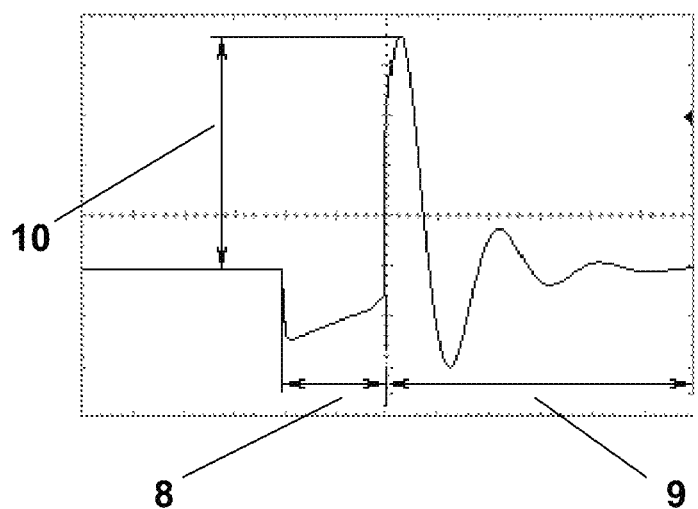
FIG. 2 is an example of stimulus.
Figure 3:
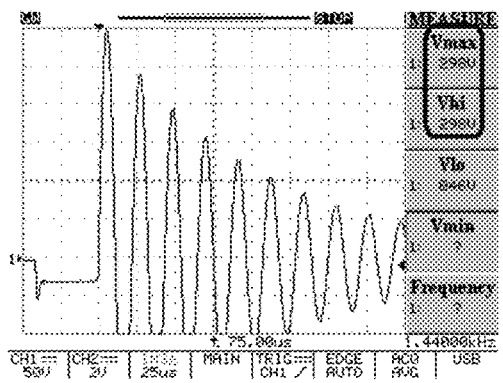
FIG. 3 illustrates a stimulus waveform before the electrodes are applied on a biological object.
Figure 4:
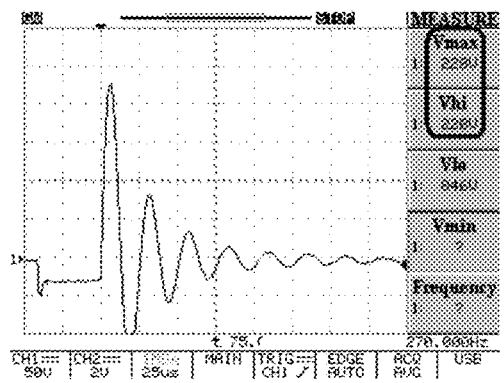
FIG. 4 illustrates a stimulus waveform immediately after the electrodes are applied on a biological object.
Figure 5:
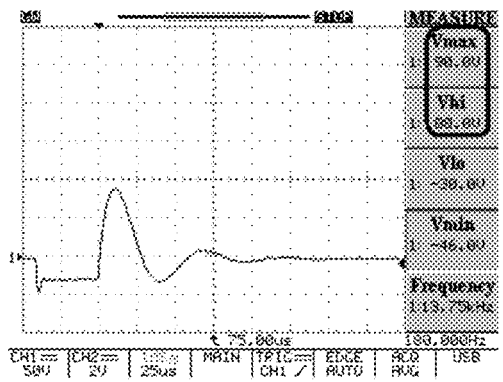
FIG. 5 illustrates a stimulus waveform 5 seconds after the electrodes are applied on a biological object.

FIG. 2 shows an example of the stimulus waveform: 8—first stage of the stimulus (pumping), 9—second stage of the stimulus (free oscillation), 10—amplitude of the first pulse of the second stimulus stage (hereinafter—stimulus amplitude).

a. The SCENAR Device Operates as Follows.

Initially, the switch 4 is open. When the switch 4 is closed, the first stage 8 of the stimulus generation starts, during which the voltage from the power source 3 is applied to the inductive energy storage unit 1, which makes the linearly increasing current flow through it and thereby makes the electromagnetic energy accumulate in the inductive energy storage unit 1. I.e, at this time, the energy is pumped into the inductive energy storage unit 1, hence the other name for the first stage of the stimulus is "pumping".

At this stage, the inductive energy storage unit 1 with the active resistance 2, and the power source 3 connected in series with the switch 4 are connected in parallel with the interelectrode tissues 7. Since the internal resistance of the power source 3 and the switch 4 (several Ohms units, these resistances are not shown in the diagram because of their small values) is much less than the impedance of the interelectrode tissues 7, the stimulus waveform during the first stage is almost independent of the interelectrode tissue impedance.

After the accumulated energy reaches a preset value, the inductive energy storage unit 1 is disconnected from the power source 3, breaking the switch 4. This starts the second stage 9 of the stimulus generation, during which the energy accumulated by the inductive energy storage unit 1 in the previous stage is transferred through the electrodes 5 and 6 to the tissue of the biological object 7 and excites free electrical oscillations in the oscillating circuit formed by the inductance of the inductive energy storage unit 1 and the impedance of the interelectrode tissues 7. Now a small internal resistance 2 of the inductive storage 1 is connected in series with the impedance of the interelectrode tissues 7, therefore, the oscillation waveform is entirely dependent on the impedance of the interelectrode tissues 7 and the inductance of the inductive storage 1.

Another name for the second stage is "free oscillation". Exciting oscillation this way is known as "shock excitation", and the respective circuit is called "ringing circuit".

The stimulus amplitude 10 depends both on the energy accumulated during the first stage (that is, on the first stage duration 8) and on the impedance parameters of the interelectrode tissues 7.

The described stages follow one another during the entire procedure of SCENAR-therapy.

The proposed method of electric stimulation shall be implemented as follows.

The electrodes 5 and 6 of the SCENAR device are applied on the tissue of the biological object, and the SCENAR device is used to generate two-stage stimuli on the electrodes 5 and 6 as described above.

Since biological tissues contain a complex aggregate of aqueous solutions, when they come into contact with the electrodes 5 and 6, a potential difference (a double electric layer) appears on the border between the metal electrodes 5, 6 and the said tissues, called the electrode potential (see "Methods of Clinical Neurophysiology", edited by V. B. Grechina, Leningrad, Nauka, 1977, pp. 7-8).

As a result of the double electric layer appearance and the influence of stimuli supplied through the electrodes 5 and 6 on the biological object's tissues, their impedance changes with time. This, in turn, leads to variation in time of the electrical oscillation parameters in the said ringing circuit.

Figure 6:
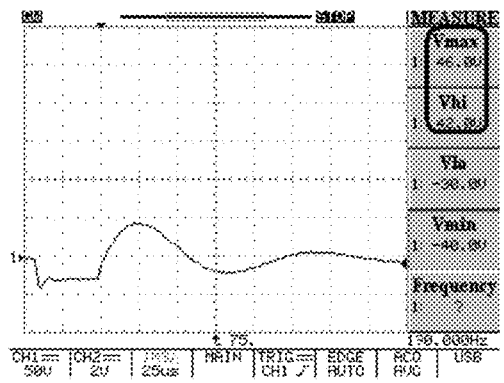
FIG. 6 illustrates a stimulus waveform 30 seconds after the electrodes are applied on a biological object.

From the oscillograms of the actual waveform of stimuli on the patient's skin as shown in FIGS. 3-6 (the results of an automatic measurement of the stimulus amplitude are outlined in the upper right corner) at a constant stimulus energy, it is clear that the maximum stimulus amplitude that reached 300 V at no-load (FIG. 3, before application) reduces to 228 V immediately after applying the electrodes on the tissue (FIG. 4), then drops to 90 V after 5 seconds (FIG. 5), and after the following 25 seconds it drops to 42-46 V (FIG. 6).

The SCENAR practice shows that such a significant (more than five times) change in the maximum amplitude of stimuli does not affect the patient's subjective sensations during the stimulation. Patient's sensations depend on the stimulus energy, which is determined by the pumping duration.

The therapeutic effect of electric stimulation also depends on the stimulus energy, but an increase in the energy of a single stimulus is not always acceptable, as it may cause a discomfort and even pain in the patients. Enhancing the therapeutic effect by increasing the stimulus frequency, when their energy is kept constant, is not always possible, since the well-known 'habituation effect' (also known as accustomization) increases with increasing stimulus frequency, thus reducing the effectiveness of electric stimulation (some ways to control the "habituation effect" in traditional electrotherapy are described, for example, in RU patent 2017508 A61N1/36, published on 15 Aug. 1994 and RU patent 2054954 A61N1/36, published on 27 Feb. 1996).

Therefore, reasonable means for increasing the intensity of electric pulse stimulation and the therapeutic effect it provides, at constant stimulus energy and frequency, is to generate stimulus bursts instead of a single stimulus, in each burst the stimuli follow one another at a repetition rate that is much higher than that of the bursts. In this case, the total energy of the burst increases according to the number I of the stimuli it contains (the term 'intensity' is well-established), which increases the effectiveness of electric stimulation, and the patient's "habituation" to the increase in the number of pulses per unit time (equivalent frequency) is not observed, which is provided by the low burst repetition rate.

With the increase in the number of stimuli in bursts, the subjective sensation of electric stimulation intensifies much more slowly than the number of stimuli increases, which provides more opportunities for individual adjustment of stimulus parameters for each patient during SCENAR therapy.

Figure 7:
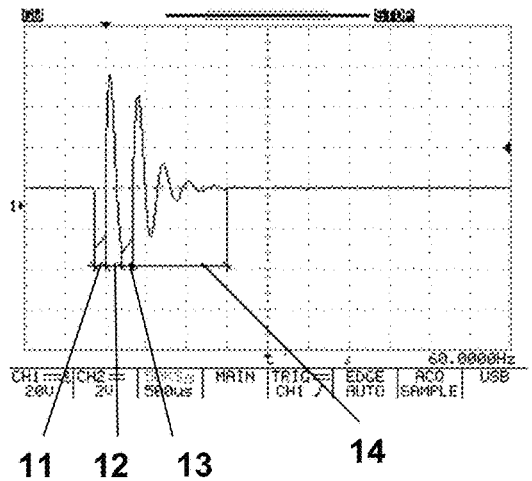
FIG. 7 illustrates the waveform of the stimulus burst with the number of stimuli I=2 and a gap G=200 μs.
Figure 8:
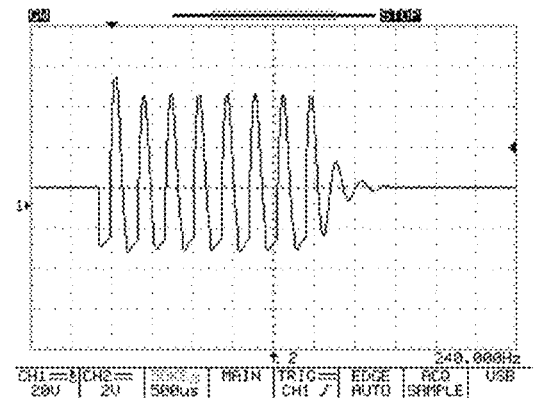
FIG. 8 illustrates the waveform of the stimulus burst with the number of stimuli I=8 and a gap G=200 μs.
Figure 9:
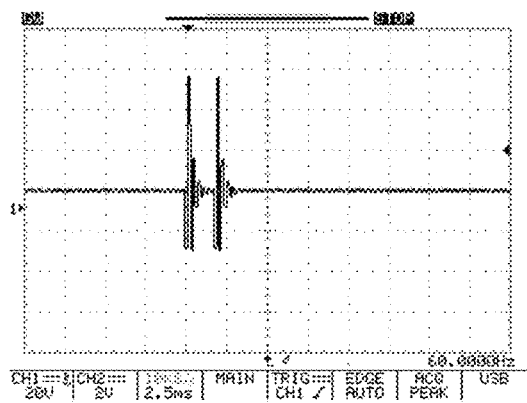
FIG. 9 illustrates the waveform of the stimulus burst with the number of stimuli I=2 and a gap G=1600 μs.
Figure 10:
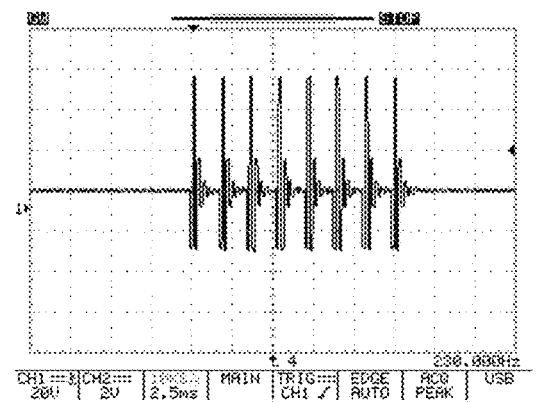
FIG. 10 illustrates the waveform of the stimulus burst with the number of stimuli I=8 and a gap G=1600 μs.

FIGS. 7-10 illustrate oscillograms of SCENAR-stimuli at a constant RC-circuit load for the bursts with the number of stimuli I=2 and I=8 with minimum and maximum gaps (time intervals between stimuli in a burst, the accepted designation is Gap) for SCENAR-NT devices $Gap_{min}$=200 µs, $Gap_{max}$=1600 µs. FIG. 7 shows: 11—pumping of the first stimulus, 12—incomplete free oscillation (with a gap of 200 µs), 13—pumping of the second stimulus, 14—fully completed free oscillation. For this load with short gaps, free oscillation 12, which started immediately after the end of pumping the first stimulus 11, does not have time to completely fade out, as the pumping 13 of the next stimulus interrupts the oscillation. The low impedance of the pumping circuit (see above the description of SCENAR device operation) shunts (damps) the oscillating circuit, and the electrical oscillations in the circuit almost immediately cease, and due to this, part of the energy of the previous stimulus is wasted. This effect is clearly seen in the pairwise comparison of FIGS. 7 and 9, and FIGS. 8 and 10, respectively: for a small gap, the amplitude of the second and subsequent stimuli is much smaller than that of the first stimulus, and for a large gap, when the free oscillations completely fade out before the next pumping, the amplitudes of all stimuli in the burst are the same. The free oscillations of the last stimulus in the burst always have time to fade out before the next burst of stimuli begins.

The stimulus interference may result in a decreased effectiveness of the electrical stimulation, and, accordingly, a decreased therapeutic effect of SCENAR treatment.

This interference of the adjacent stimuli in a burst can be eliminated by matching the start of each new pump with the current phase of free oscillations.

Figure 11:
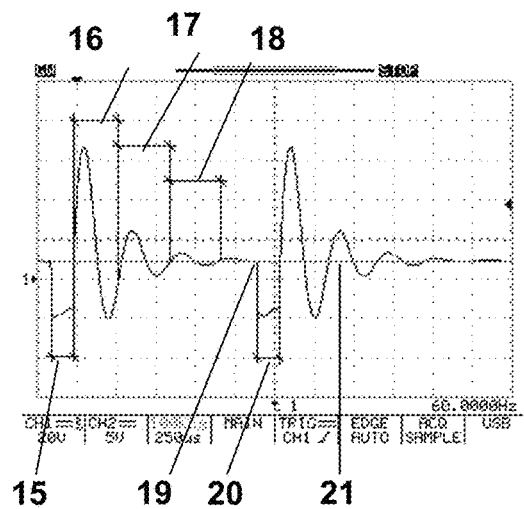
FIG. 11 illustrates the waveform of the stimulus burst with the number of stimuli I=2 when the second stimulus is pumped after the first stimulus oscillations complete.

FIG. 11 shows a burst of two stimuli, where:
pumping of the first stimulus 15,
first, second and third oscillations (16, 17 and 18, respectively) of the second stage of the first stimulus,
end of the second stage of the first stimulus 19,
pumping of the second stimulus 20,
"zero" level 21.

In the burst shown in FIG. 11, the pumping of the second stimulus begins upon completion of the free oscillations of the first stimulus (variant 1 of the matching).

Figure 12:
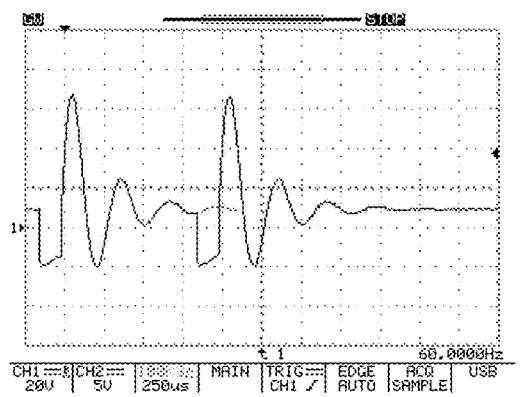
FIG. 12 illustrates the waveform of the stimulus burst with the number of stimuli I=2 when the second stimulus is pumped at the minimal third oscillation of the first stimulus.
Figure 13:
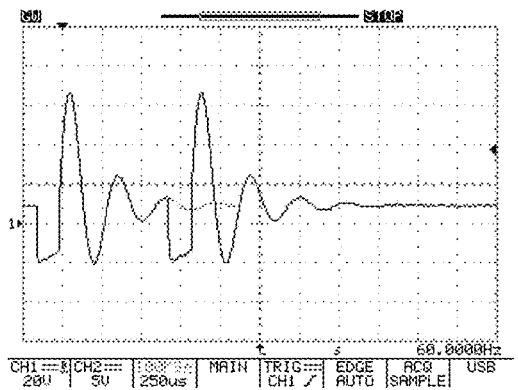
FIG. 13 illustrates the waveform of the stimulus burst with the number of stimuli I=2 when the second stimulus is pumped at the maximal third oscillation of the first stimulus.
Figure 14:
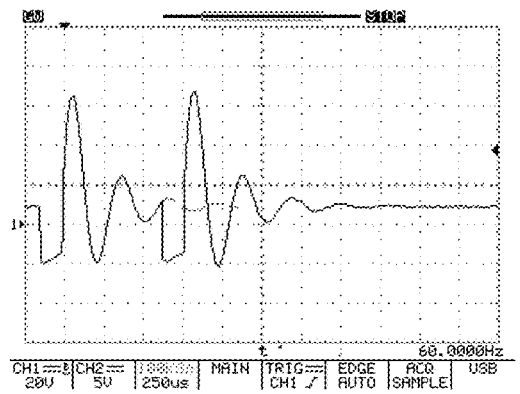
FIG. 14 illustrates the waveform of the stimulus burst with the number of stimuli I=2 when the second stimulus is pumped upon zero-crossing between the second and third oscillations of the first stimulus.

As examples of matching the start of the next pumping of the inductive energy storage unit 1 with the current phase of free oscillations, FIGS. 12-14 show the waveforms at I=2 for the other three variants of the onset of pumping of the next (second in the burst) stimulus:

at the minimum of the third oscillation 18 (FIG. 12) (variant 2);

at the maximum of the third oscillation 18 (FIG. 13) (variant 3);

at zero-crossing between the second 17 and the third 18 oscillations (FIG. 14) (variant 4).

For clarity, FIGS. 12-14 show, in gray, the free oscillations trace for the case when the next pump phase of the inductive energy storage unit 1 does not start.

In SCENAR-therapy using the matching of onset of every new pumping with the current phase of free oscillations, it was found that, although the waveforms of stimuli differ insignificantly, all patients report a distinct difference in their subjective perception of electric stimulation during SCENAR-therapy. Most of them describe their sensations as "more prickly" for the variants 3 and 4 (FIGS. 13 and 14) and "less prickly" for the variants 1 and 2 (FIGS. 11 and 12), and some patients describe their feelings as "stronger" for the variants 3 and 4 and "weaker" for the variants 1 and 2. Hence, from the patient's sensations it follows that the variants 1 and 2 are more advantageous as they provide a more comfortable SCENAR-stimulation.

On the other hand, "more prickly" (FIGS. 13 and 14) stimuli can also be used to enhance the functionality of electric stimulation, for example, when a stronger response to the stimulation needs to be obtained without increasing its total energy.

Thus, by controlling the onset of pumping of the next stimulus in the burst taking into account the current phase of free oscillations, as well as by selecting the reasonable number of stimuli in the burst, one can significantly increase the total energy of electric stimulation, speed up the body's response to it and generally increase the therapeutic effect of SCENAR-therapy keeping it comfortable to the patients.

For adaptive control of stimuli according to changed impedance of biological tissues, the proposed method of SCENAR-therapy watches the parameters of electrical oscillations (phase duration and number of oscillations, duration and degree of oscillation fadeout, etc.) excited in the oscillating circuit, and the stimuli are adjusted by controlling the parameters of stimuli in the bursts and/or burst repetition rate based on the current values of the parameters of electric oscillations.

The oscillograms in FIGS. 11 through 14 are taken at a constant load simulating the interelectrode impedance. In reality, for the reasons mentioned above, the interelectrode impedance continuously varies. In order to provide a reasonable pumping onset with respect to free electric oscillations, the parameters of these oscillations need to be continuously monitored. Otherwise, the effectiveness of electrical stimulation may decrease or patients may experience uncomfortable sensations. Simultaneously with controlling the onset of pumping, one may also control other parameters of the stimuli in the bursts (number I and/or the stimulus waveform) and/or the repetition rate of stimulus bursts, as they also contribute a lot to the effectiveness of the electric stimulation.

Furthermore, one may also control the waveform and/or amplitude of each individual stimulus in a burst. For example, if the number of stimuli in a burst exceeds 1, one can increase the amplitude of the second and the subsequent stimuli from the minimum or, for example, from the half of the preset level to this level, which will give a "softer" sensation than a burst of stimuli of constant amplitude and allow control the amplitude in the larger range. Since the stimulus waveform depends on the interelectrode impedance, it can be controlled, for example, by connecting the damping RC circuits with various parameters in parallel to the electrodes. This allows to control the waveform of each individual stimulus in a burst, changing the "sharpness" of senses also by changing the level of damping.

The above stimulus parameters can also be controlled both in the current burst, and in the following, and/or in any of the subsequent stimulus bursts, or in several subsequent stimulus bursts in a row. The same applies to the repetition rate of stimulus bursts, which can be controlled depending on the parameters of free oscillations—for the next stimulus burst or for several subsequent bursts.

According to the proposed method of SCENAR-therapy, there are three ways as follows to monitor free oscillation parameters and to carry out adaptive control of stimuli.

The first variant includes the direct monitoring of the current oscillation where the parameters of free oscillations are measured during the action of each stimulus of the current burst. Based on the results of these measurements, the reasonable values of the parameters of the current stimulus burst (onset of the next stimulus in the burst relative to the current phase of the oscillations and/or the number I and/or the stimulus waveform) are set and/or the repetition rate of subsequent stimulus bursts and/the parameter of the subsequent stimulus bursts. In doing this, the same parameter settings are used for all stimuli in a burst, or the parameters of each stimulus in a burst are controlled separately.

This variant provides the best accuracy of free oscillation parameters evaluation, since it allows measuring the parameters in real time and, thus, to take into account all actual changes in the interelectrode impedance.

To perform these measurements in real time, a high-speed analog-to-digital converter (ADC) is required, and for timely generation of the next stimulus in a burst (for example, immediately after zero-crossing) a high-performance microcontroller is required.

In addition, since the oscillations waveform varies continuously (including during each oscillation), then to adjust the onset of the next pump, the mode changes need to be predicted. This further increases the microcontroller performance requirements as well as software requirements.

Therefore, there is another way (variant 2) for monitoring the parameters of free oscillations and adaptive stimulus control. In this variant the said parameters are measured while the biological tissues are exposed to the last stimulus in each burst. During the pause between the previous and next bursts, one sets the reasonable values of the parameters in the subsequent stimulus burst (the onset of the next stimulus in the burst against the oscillation phase and/or the number I and/or the stimulus waveform) and/or the repetition rate of the subsequent stimulus bursts and/or the parameters of subsequent stimulus bursts.

An advantage of this variant is that the oscillatory process of the last stimulus of each burst is always completed without any interference, as it cannot be overlapped by the first stimulus of the next burst. Now, after these oscillations are completed, their parameters can be precisely estimated, so there is no need in prediction. Due to this, compared with the previous variant, the requirements to microcontroller performance are now significantly lower, and the software is simpler. Instead of a fast ADC, one can use a simpler unit—a comparator, which provides a direct measurement of the number of oscillations and zero-crossings for these oscillations.

When the repetition rate of the stimulus bursts is reduced to 20-30 Hz (i.e. the pause between the bursts exceeds 30 ms), during the pause the interelectrode impedance changes noticeably, which can impair the accuracy of matching the onset of the next stimulus in the burst with the current phase of oscillations and/or adjusting the repetition rate of the subsequent stimulus bursts and/or stimulus parameters in subsequent bursts, which may result in a lower effectiveness of the electric stimulation and/or less comfortable SCENAR-therapy.

Therefore we propose a third variant for monitoring the oscillation parameters and adaptive control, where after the end of the last stimulus of each burst but prior to the next burst (i.e., in a pause between two adjacent bursts), a single probing stimulus is generated.

Figure 15:
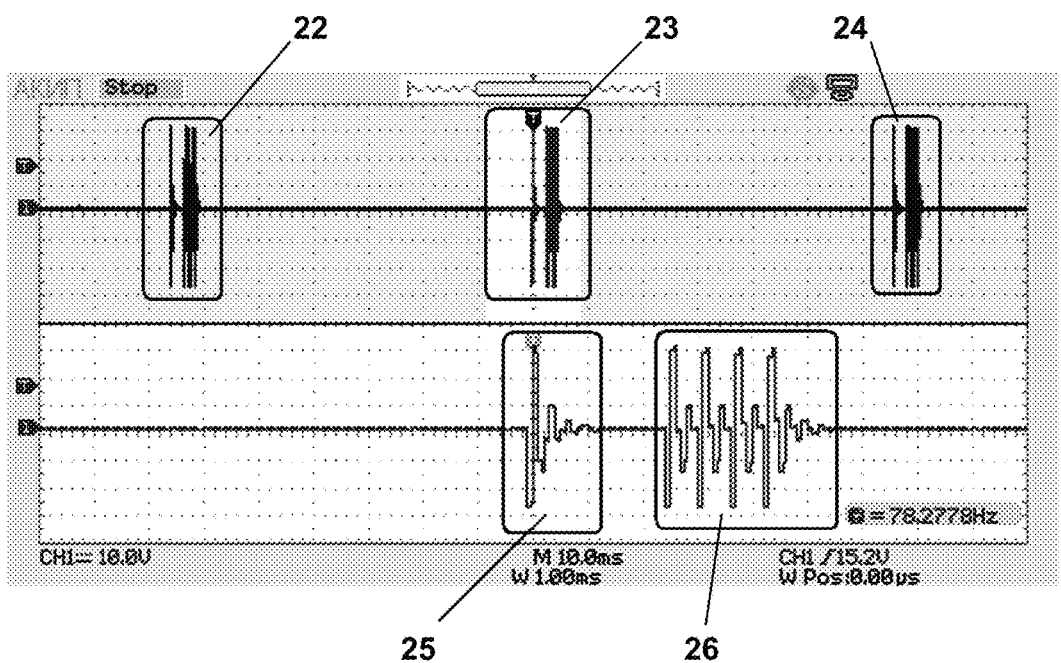
FIG. 15 illustrates the waveform of the stimulus burst with a probing stimulus between the bursts.

FIG. 15 gives an example of such stimuli. On the upper oscillogram there are three stimulus bursts 22, 23 and 24, and the stimulus burst 23 is highlighted in light background, which is shown enlarged (extended) on the lower oscillogram. Here, a probing stimulus 25 is well visible, whose oscillating process is fully completed before the basic burst of pulses 26 begins.

Here the oscillation parameters of the said probing stimulus are measured and the onset of the next stimulus in the burst and/or the parameters of stimuli in subsequent bursts and/or the repetition rate of subsequent stimulus bursts and/or stimulus parameters included in the subsequent stimulus burst or any of the subsequent stimulus bursts are set based on these measurements.

The probing stimulus must be located as close as possible to the next stimulus burst and at the distance that ensures the completion of its oscillations before the first stimulus of the next burst begins.

This variant provides high precision of determining the onset of pumping when the stimuli in the next burst are generated at low repetition rates of stimulus bursts.

Each of the presented variants for monitoring the oscillation parameters and adaptive control of stimuli has its own optimal field of application.

The first variant is the most universal and provides highly precise control, but at the same time it is hardware and algorithms intensive and, in general, requires a high-speed ADC and a high-performance microcontroller.

The second variant is the easiest to be implemented, the least software, algorithm, and microcontroller performance intensive, and allows using the simplest comparator instead of the ADC.

The third variant is more complicated than the second, but simpler than the first variant in implementation, and provides more precise control when stimuli are generated in the burst for low repetition rates of stimulus bursts.

All the three variants can set the same parameter for all the stimuli of the next burst, or control the parameters of each stimulus in the next burst separately.

Since the change in the parameters of free oscillations is caused by variations of the interelectrode impedance, which, in its turn, depends on the local and general responses of the body to the stimulation, then the change in the oscillation parameters can also serve as a criterion for the exposure duration. For example, if there is no change in one or more of these parameters for some time, this means that the response to the stimulation has stabilized, and the stimulation can be terminated.

Furthermore, a coil or transformer, or autotransformer, can be used as an inductive energy storage unit in each of the three variants.

Figure 16:
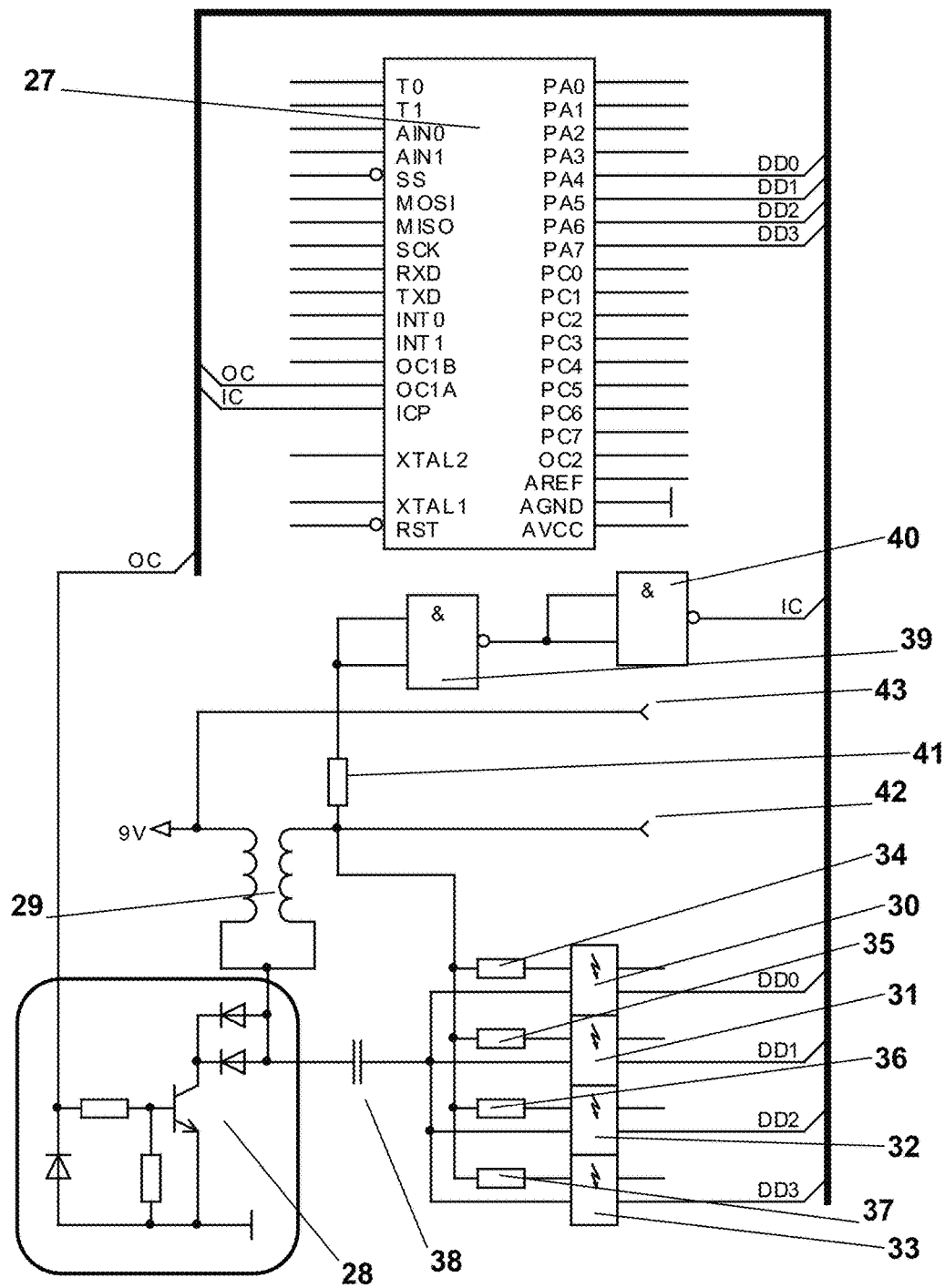
FIG. 16 illustrates a circuit fragment for SCENAR-1-NT neuroadaptive electric stimulator.

In order to implement any of the described variants for monitoring electrical oscillation parameters and adaptive stimulus control, one can use serially produced SCENAR devices, for example, the SCENAR-1-NT device, whose circuit fragment is illustrated in FIG. 16 (supply circuits, interface circuits and other secondary circuits are not shown on the fragment).

The microcontroller 27 processes key presses, display and audible indication, generates control pulses, measures the parameters of free oscillations, determines the next pump onset, controls the circuits influencing the waveform of stimuli, etc.

The switch 28 with protective circuits (corresponding to the switch 4 of the functional circuit in FIG. 1) controls the inductive energy storage unit 29 made as an autotransformer (corresponds to the inductive energy storage unit 1 with the internal resistance 2 of the functional diagram in FIG. 1).

The switches 30-33, together with the resistors 34-37 and the capacitor 38, form switchable RC circuits and control the waveform of the stimuli (damping), as described above.

The elements 39 and 40 make a comparator, which distinguishes zero crossings of the free oscillations of stimuli. The signal is supplied through the resistor 41 from the active electrode 42 to the comparator input. The passive electrode 43 is connected to the supply circuits.

Figure 17:
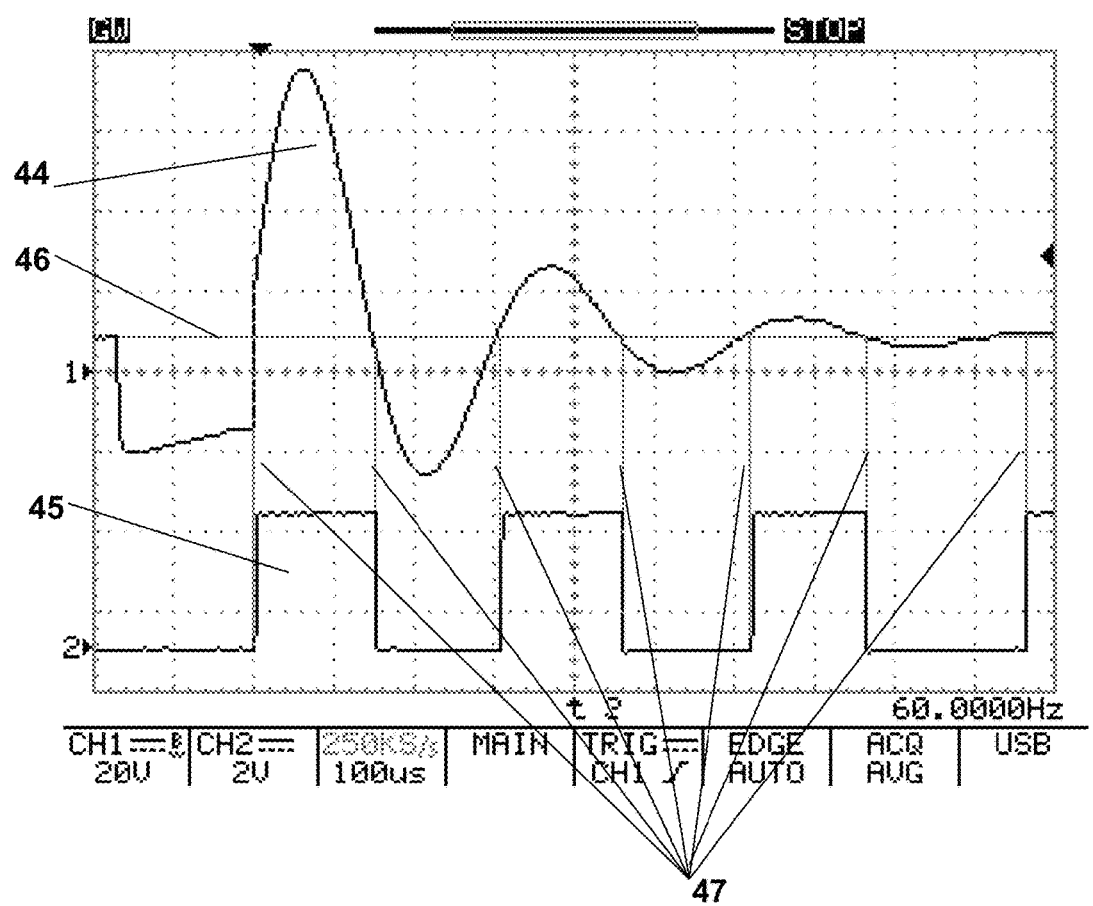
FIG. 17 is the oscillogram of stimuli and comparator output for the SCENAR-1-NT neuroadaptive electric stimulator.

FIG. 17 shows the stimulus waveform 44 at a load simulating the interelectrode impedance and the output signal 45 of the comparator 40.

Figure 18:
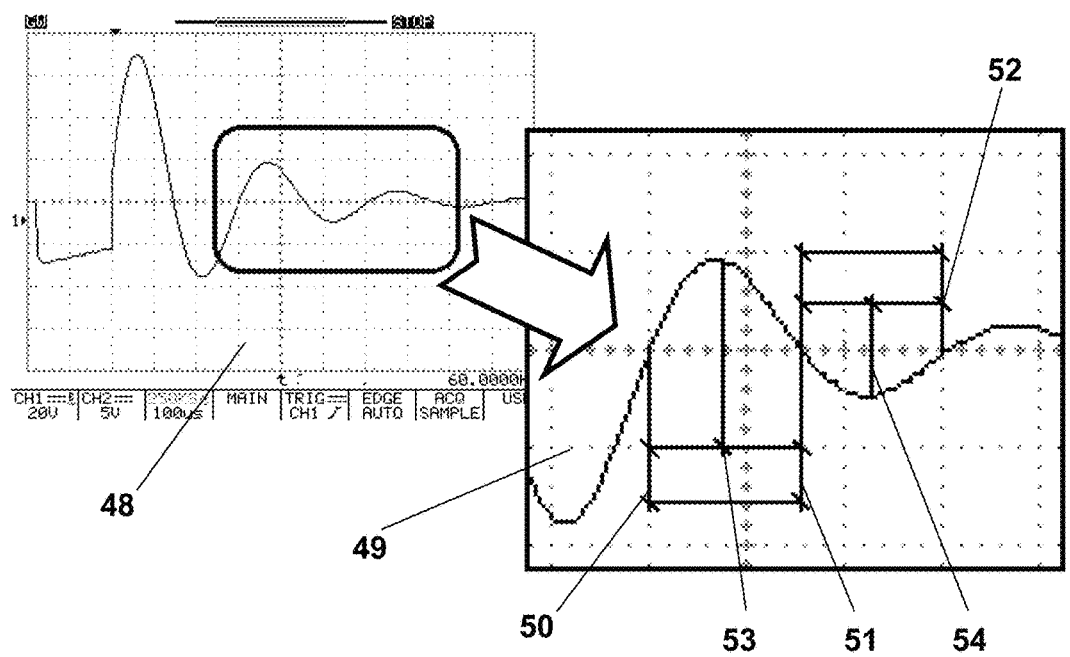
FIG. 18 is an example of determining the oscillation minimum and maximum points using the time of the neighboring zero-crossings.

On the upper oscillogram, the zero line 46 is shown in gray—an approximate level of the comparator switching. Vertical lines 47 show the moments of these switchings. Thus, the output signal of the comparator directly provides information on the oscillation zero-crossings. The moments when the oscillations reach the minimum and maximum can be determined using simple calculations (half-sum of the times of the corresponding zero-crossings). FIG. 18 explains the idea of such calculations. For example, the second oscillation is highlighted on the oscillogram 48 and this oscillation is shown enlarged in the box 49. The beginning of the second oscillation, its middle and its end are denoted by 50, 51 and 52 respectively. Half-the-time intervals between the beginning and the middle, as well as between the middle and the end of this oscillation are denoted by 53 and 54 respectively. These moments, as seen in the box 49, correspond to the maximum (53) and minimum (54) of the amplitude of the second oscillation and are calculated by the microcontroller as a half-sum of the times of the zero-crossings 50 and 51, and 51 and 52, respectively.

Thus, the SCENAR-1-NT device without any changes in the circuitry makes it possible to implement the second and third variants of the proposed method. For the first variant, the comparator should be replaced by an analog-to-digital converter with a conversion time of less than 1 μs, connected to the microcontroller via a parallel or serial interface (for example, MAX153).

The proposed method of electric stimulation provides the adaptive control of stimuli based on the ongoing values of the electrical oscillation parameters. Doing so provides a better adaptation of the stimulating electrical pulse to the functional condition of the stimulated tissues of the biological object, thereby increasing the therapeutic effect of electric stimulation and providing the necessary level of comfort for patients when performing SCENAR therapy.

The proposed method can be used in existing as well as in newly created devices to provide a general regulation and to treat a wide range of diseases, including pain relief, faster burn and fracture healing, as well as rehabilitation after physical stress and injuries.

What is claimed is:

1. A method for adaptive electric stimulation of a living body, comprising:
    applying electrodes on a the living body's tissues,
    transmitting through said electrodes one or more bursts of two or more electrical stimuli,
        said two or more electrical stimuli being generated using an inductive energy storage unit,
        said inductive energy storage unit comprising an inductance coil or a transformer or an autotransformer,
        each electrical stimulus comprising:

a pumping stage to charge said inductive energy storage unit, and a stage comprising free oscillations, said free oscillations arising in an oscillation circuit formed by an inductance of the inductive energy storage unit and an impedance of interelectrode tissues, measuring free oscillation parameters during a current electrical stimulus in a current burst, determining an optimal stimulus exposure duration and optimal stimulus parameters based on the measured free oscillation parameters, and controlling one or more parameters of a next stimulus in the current burst or any subsequent bursts based on one or more previously measured free oscillation parameters.

2. The method of claim 1, wherein the controlled stimulus parameter is a number of stimuli in the current burst or any subsequent bursts.

3. The method of claim 1, wherein the controlled stimulus parameter is a time interval between adjacent stimuli in the current burst or any subsequent bursts.

4. The method of claim 1, wherein the controlled stimulus parameter is a waveform, including an amplitude and polarity, of each stimulus in the current burst or any subsequent bursts.

5. The method of claim 1, wherein the controlled stimulus parameter is a repetition rate of subsequent bursts.

6. The method of claim 1, wherein the controlled stimulus parameter is an exposure duration.

7. The method of claim 1, wherein each electrical stimulus further comprises a zero level.

8. A method for adaptive electric stimulation of a living body, comprising:

applying electrodes on the living body's tissues, transmitting through said electrodes one or more bursts of two or more electrical stimuli, said two or more electrical stimuli being generated using an inductive energy storage unit, said inductive energy storage unit comprising an inductance coil or a transformer or an autotransformer, each electrical stimulus comprising:

a pumping stage to charge said inductive energy storage unit, and a stage comprising free oscillations, said free oscillations arising in an oscillation circuit formed by an inductance of the inductive energy storage unit and an impedance of interelectrode tissues, measuring free oscillation parameters of a last electrical stimulus in the current burst, determining an optimal stimulus exposure duration and optimal stimulus parameters based on the measured free oscillation parameters, and controlling one or more parameters of stimuli in any subsequent bursts based on previously measured free oscillation parameters.

9. The method of claim 8, wherein the controlled stimulus parameter is a number of stimuli in any subsequent bursts.

10. The method of claim 8, wherein the controlled stimulus parameter is a time interval between adjacent stimuli in any subsequent bursts.

11. The method of claim 8, wherein the controlled stimulus parameter is a waveform, including an amplitude and a polarity, of each stimulus in any subsequent bursts.

12. The method of claim 8, wherein the controlled stimulus parameter is a repetition rate of subsequent bursts.

13. The method of claim 8, wherein the controlled stimulus parameter is an exposure duration.

14. The method of claim 8, wherein the controlled stimulus parameter is a time interval between adjacent stimuli in any subsequent bursts.

15. The method of claim 8, wherein each electrical stimulus further comprises a zero level.

16. A method for adaptive electric stimulation of a living body, comprising:

applying electrodes on the living body's tissues, transmitting through said electrodes one or more bursts of two or more electrical stimuli, said two or more electrical stimuli being generated using an inductive energy storage unit, said inductive energy storage unit comprising an inductance coil or a transformer or an autotransformer, each electrical stimulus comprising:

a pumping stage for charging said inductive energy storage unit, and a stage comprising free oscillations, said free oscillations arising in an oscillation circuit formed by an inductance of the inductive energy storage unit and an impedance of interelectrode tissues, generating a probing stimulus after an end of a previous burst and before a beginning of a subsequent burst, measuring free oscillation parameters of said probing stimulus, determining an optimal stimulus exposure duration and optimal stimulus parameters based on the measured free oscillation parameters, and controlling one or more parameters of stimuli in any subsequent bursts based on previously measured free oscillation parameters of said probing stimulus.

17. The method of claim 16, wherein the controlled stimulus parameter is a number of stimuli in any subsequent bursts.

18. The method of claim 16, wherein the controlled stimulus parameter is a time interval between adjacent stimuli in any subsequent bursts.

19. The method of claim 16, wherein the controlled stimulus parameter is a waveform, including an amplitude and a polarity, of each stimulus in any subsequent bursts.

20. The method of claim 16, wherein the controlled stimulus parameter is a repetition rate of subsequent bursts.

21. The method of claim 16, wherein the controlled stimulus parameter is an exposure duration.

* * * * *